United States Patent
Takekoshi

(10) Patent No.: US 8,537,971 B2
(45) Date of Patent: Sep. 17, 2013

(54) IMAGING APPARATUS AND CONTROL METHOD THEREOF

(75) Inventor: Koji Takekoshi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/555,275

(22) Filed: Jul. 23, 2012

(65) Prior Publication Data

US 2012/0288064 A1    Nov. 15, 2012

Related U.S. Application Data

(63) Continuation of application No. 12/841,307, filed on Jul. 22, 2010, now Pat. No. 8,254,523.

(30) Foreign Application Priority Data

Jul. 31, 2009 (JP) ................................. 2009-180050

(51) Int. Cl.
 *H05G 1/64* (2006.01)
(52) U.S. Cl.
 USPC ......................................................... 378/98.2
(58) Field of Classification Search
 USPC .................. 378/62, 98.2, 98.8, 98.11, 98.12; 250/370.08, 370.09; 382/131, 298; 345/660
 See application file for complete search history.

(56) References Cited

U.S. PATENT DOCUMENTS

| 6,075,256 A | 6/2000 | Kaifu et al. .................... 257/53 |
| 6,731,783 B2 | 5/2004 | Tsujii ............................ 382/132 |
| 7,076,027 B2 | 7/2006 | Matsumoto .................. 378/98.8 |
| 7,511,721 B2 | 3/2009 | Takekoshi ..................... 345/630 |
| 8,102,418 B2 | 1/2012 | Kojima ........................... 348/80 |
| 8,254,523 B2 * | 8/2012 | Takekoshi .................... 378/98.2 |
| 2011/0075812 A1 | 3/2011 | Takekoshi et al. ........... 378/98.8 |

FOREIGN PATENT DOCUMENTS

| JP | 2786849 | 8/1998 |
| JP | 2009-159497 A | 7/1999 |
| JP | 3066944 | 7/2000 |
| JP | 3326914 | 9/2002 |
| JP | 3554172 | 8/2004 |
| JP | 2005-124620 | 5/2005 |
| JP | 4042414 | 2/2008 |
| JP | 2009-128648 A | 6/2009 |

* cited by examiner

*Primary Examiner* — Courtney Thomas
(74) *Attorney, Agent, or Firm* — Fitzpatrick, Cella, Harper & Scinto

(57) ABSTRACT

An imaging apparatus having an X-ray detector and an image display unit comprises first and second display magnification calculation units and a selection unit. The first display magnification calculation unit receives information of the detected image size, a binning condition and a display frame size, and thereby calculating a first display magnification so as to maximize a display area of the detected image. The second display magnification calculation unit temporarily changes the received binning condition, and by using the temporarily changed binning condition and the received detected image size, and calculates a second display magnification so as to maximize a display area. The selection unit selects the first display magnifications and the temporarily change binning condition if the first display magnification is closer to one and the second display magnification with one.

5 Claims, 9 Drawing Sheets

F I G. 1
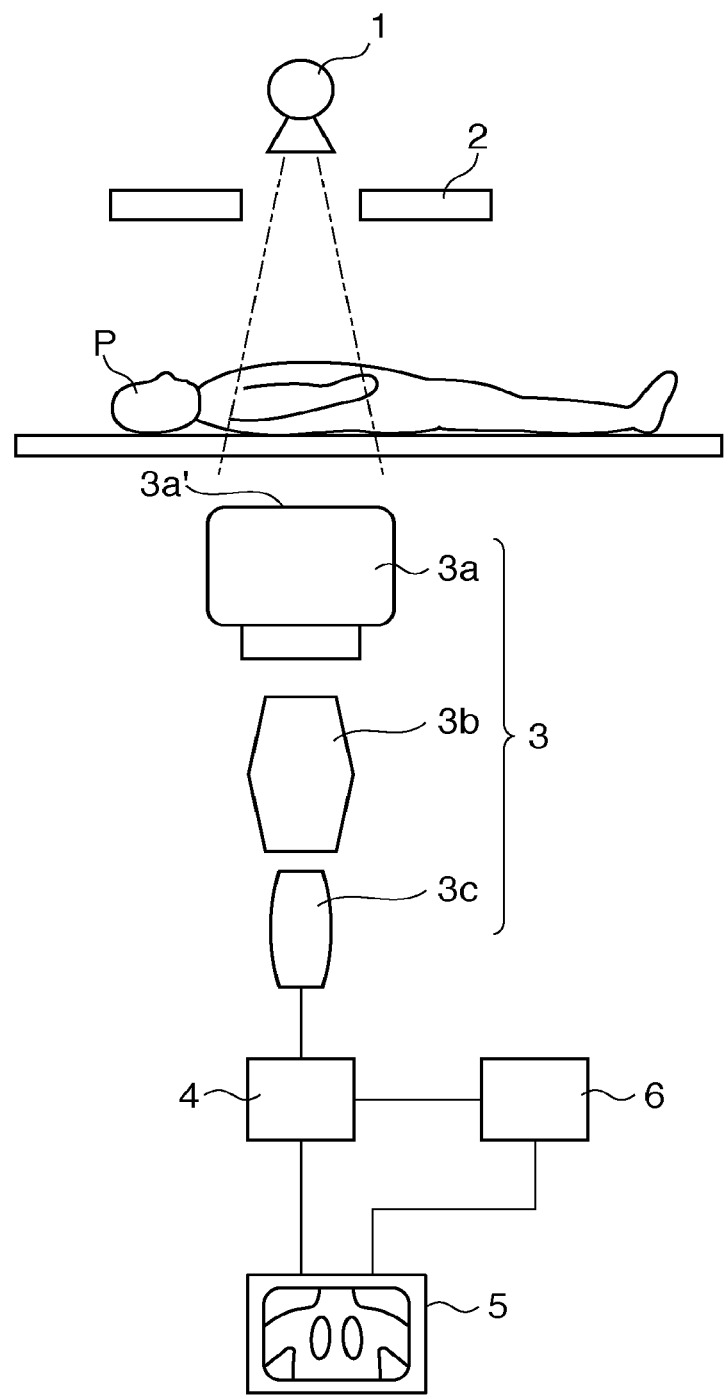

FIG. 9
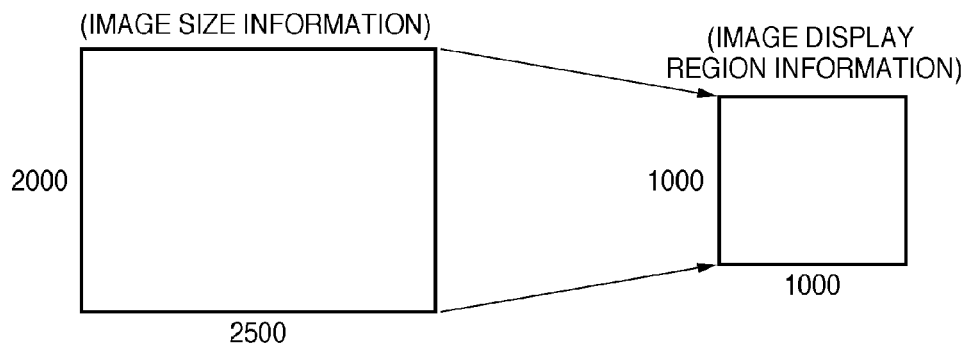
FIG. 10
|  | REGION | RESOLUTION | FRAME RATE | X-RAY DOSE |
|---|---|---|---|---|
| POSITIONING TRANSMISSION | WIDE | LOW | HIGH | LOW |
| GENERAL CAPTURING | — | HIGH | LOW | LOW |
| HEART PORTION | NARROW | HIGH | HIGH | LOW |
| HEAD PORTION | WIDE | HIGH | — | LOW |
FIG. 11
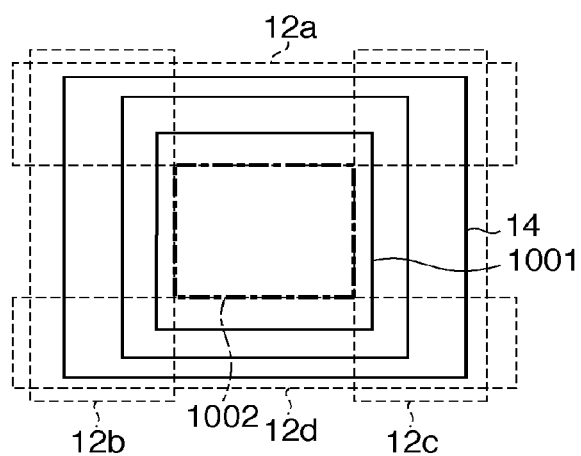

FIG. 12

| READING REGION | BINNING | 5fps | 15fps | 30fps |
|---|---|---|---|---|
| 14inch × 17inch | 1×1 | POSSIBLE | — | — |
| | 2×2 | POSSIBLE | POSSIBLE | — |
| 12inch × 12inch | 1×1 | POSSIBLE | — | — |
| | 2×2 | POSSIBLE | POSSIBLE | — |
| 9inch × 9inch | 1×1 | POSSIBLE | POSSIBLE | — |
| | 2×2 | POSSIBLE | POSSIBLE | POSSIBLE |
| | 4×4 | POSSIBLE | POSSIBLE | POSSIBLE |

FIG. 13

| PRIORITY | UNCHANGEABLE | CHANGEABLE | |
|---|---|---|---|
| RESOLUTION | FIXED | BINNING CONDITION CHANGE | |
| READING AREA (DETECTED IMAGE SIZE) | FIXED | NARROW AREA PRIORITY | WIDE AREA PRIORITY |
| FRAME RATE | FIXED | LOW FRAME RATE PRIORITY | HIGH FRAME RATE PRIORITY |

IMAGING APPARATUS AND CONTROL METHOD THEREOF

RELATED APPLICATIONS

This application is a continuation of application Ser. No. 12/841,307, filed Jul. 22, 2010 now U.S. Pat. No. 8,254,523, claims benefit of the filing date of that application under 35 U.S.C. §120, and claims priority benefit under 35 U.S.C. §119 of Japanese Patent Application 2009-180050, filed Jul. 31, 2009. The entire contents of both mentioned earlier applications are incorporated herein by reference.

BACKGROUND OF THE INVENTION

1. Field of the Invention

The present invention relates to a medical X-ray imaging apparatus.

2. Description of the Related Art

An image intensifier-TV system is especially utilized for fluoroscopic radiography apparatus in the area of diagnostic imaging using a medical X-ray image capture apparatus.

FIG. 1 illustrates an example of an image intensifier (hereafter "I.I")-TV system in the past. First, a subject P is irradiated with X-rays from an X-ray tube 11be through an X-ray aperture 2. Then, the transmission X-rays transmitted through the subject P are detected by a detection unit 3, and converted to an image signal, and the converted image signal is displayed as an image on a monitor 5 via an image processing means 4.

The X-rays with which the subject P is irradiated are placed via the X-ray aperture 2 so as to irradiate only a predetermined region that is required for capturing an image. The detection unit 3 converts the transmission X-rays to an optical image of visible light by I.I 3a, and guides the converted optical image to a television camera 3c via an optical system 3b, where the optical image is converted to the image signal.

The image processing means 4 converts the received image signals to digital image data. The image processing means 4 performs zoom-in and -out of the image, displacement of the image position and various computations including addition and subtraction of the image, and processing of the image. Further, a record unit 6 records and stores the digital image data before or after processing. It is possible that the record unit 6 stores a moving image which is captured by irradiating the subject P with the continuous or pulsed X-rays, or stores a still image which is captured at arbitrary timing by observing the moving image.

As mentioned above, the area which can be captured by the transmissive X-rays transmitted through the subject P impinging upon an entry surface 3a' of the I.I 3a of the fluoroscopic radiography apparatus is called a visual field size. The maximum visual field size of the normal I.I 3a is determined by the bore diameter and the visual field size can be set by switching a visual field size in a stepwise fashion. The size of the area to be captured is determined by switching the visual field size for capturing the subject P.

Further, it is possible to obtain an enlarged high-resolution optical image by setting a small visual field size. For an example of the I.I 3a, the visual field size can be switched among the sizes of 12, 9, 7.5 and 6 inches. In this case, if a 6-inch visual field size is utilized, it will be possible to perform image capture at a magnification of four times the magnification (resolution) possible with a 12-inch visual field size. Recently, a high resolution solid X-ray detection unit is proposed using a FPD (Flat Panel Detector) in lieu of the detection unit 3.

Japanese Patent No. 3066944 shows a method of acquiring the X-ray image of the subject as digital data by converting the transmissive X-ray amount transmitted through the subject to an electrical signal, where the subject is placed between an X-ray source and X-ray sensor by using FPD Japanese Patent No. 3326914 introduces an X-ray fluoroscopic apparatus which can perform an enlargement process by detecting that the image size, which is displayed on the monitor, is smaller than a predetermined size. Japanese Patent No. 4042414 also indicates a medical image processing apparatus which performs a reduction process so as to leave the region of interest.

Further, Japanese Patent No. 2786849 introduces an X-ray diagnostic apparatus which can appropriately visualize an X-ray image corresponding to a captured portion and each of fluoroscopic modes and capture modes. Japanese Patent Laid-Open No. 2005-124620 also introduces an X-ray fluoroscopic apparatus which can set aperture information in a trigger so as to obtain a requested image. Further, Japanese Patent No. 3554172 shows a radiography capture apparatus which extracts the region of exposure field from the image fully readout, and performs the image readout according to the extracted exposure field information.

However, the apparatus as mentioned above has the following problems: As for capturing the subject P, in the fluoroscope process of positioning the objective portion to be captured, a wide region and low X-ray amount are desirable and a resolution and frame rate may be compromised in some degree. In the fluoroscope process of positioning the objective portion to be captured, a high resolution and high frame rate are desirable. Once the region is established, the image in a narrow region may be often allowable. Further, in some spot captures where fluoroscopic capture, serial radiography or still image capture is performed, a high resolution may be disabled and the low frame rate may be allowable.

In any capture, the captured region of the subject P is desired to flexibly be set. For example, a clearer and higher S/N image is required when specifying a desired region (the region of interest) for fluoroscopic capture of the objective portion or spot capture using the wide region of the captured image when performing fluoroscopic image capture. For this purpose, the above setting is required when the region of interest is determined by gradually narrowing the region and capture with increasing the irradiated X-ray quantity or increasing the resolution. However, in such capture, there is a problem in that the operation becomes complicated due to the condition of X-ray irradiation, the setting of the X-ray aperture and the setting of binning having to be performed independently. Further, there is the problem that it is difficult to immediately determine whether or not the binning setting should be changed using the image information displayed on the monitor.

SUMMARY OF THE INVENTION

The present invention provides a method for displaying an image, whereby differences in image sizes and display monitors are considered, and priority is given to image quality in accordance with image capture purpose.

In order to solve these problems, the imaging apparatus having an X-ray detector of detecting transmissive X-rays passing through a subject irradiated from the imaging apparatus and an image display unit of displaying the detected image by the X-ray detected by the detector, comprising: a first display magnification calculation unit for receiving information of the detected image size which is a size of a reading area of the detector, a binning condition and a display frame size of the image display unit, and thereby calculating a first display magnification so as to maximize a display area of the detected image corresponding to the display frame size and not to exceed the size of the display frame size; a second display magnification calculation unit for temporarily changing the received binning condition, and by using the temporarily changed binning condition and the received detected image size, calculating a second display magnification so as to maximize a display area of the detected image corresponding to the display frame size and not to exceed the size of the display frame size; a selection unit for selecting the second display magnification and the temporarily change binning condition if the second display magnification is closer to one when comparing the first display magnification and the second display magnification with one, and selecting the first display magnification and the received binning condition if the first display magnification is closer to one when comparing the first display magnification and the second display magnification with one.

The present invention can provide the display which is considered the image priority corresponding to the capture purpose.

Further features of the present invention will become apparent from the following description of exemplary embodiments (with reference to the attached drawings).

BRIEF DESCRIPTION OF THE DRAWINGS

FIG. 1 illustrates a block diagram of the medical image capture apparatus that has existed in the past.

FIG. 9 shows an example of the relationship between image size information and image display region information.

FIG. 10 shows examples of priority in the operation.

FIG. 11 shows a collimator aperture and a reading area.

FIG. 12 shows the relationship among reading areas of X-ray plane detector, binning conditions and frame rates.

FIG. 13 shows the relationship among resolutions, reading areas and frame rates.

DESCRIPTION OF THE EMBODIMENTS

Below is a detailed description of embodiments of the present invention with reference to the drawings.

First Embodiment

First, why capture conditions have to be determined considering priority of image or priority of frame rate as shown in this embodiment will be described.

Figure 2:
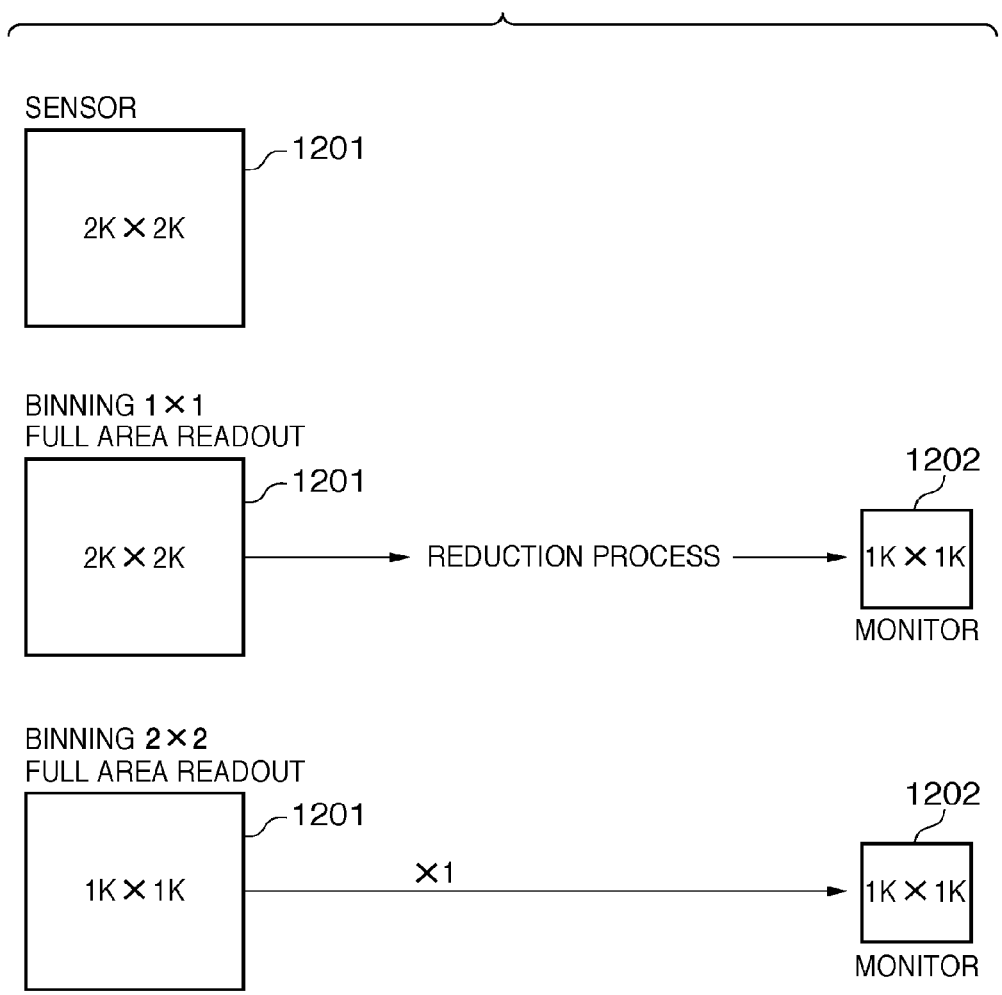
FIG. 2 shows the relationship between image display and image interpolation.

FIG. 2 illustrates general relationship between an image display and image interpolation. As shown in FIG. 2, a pixel size of a sensor 1201 is assumed 2K×2K, and a pixel size of a monitor 1202 is assumed 1K×1K. In this case, for example, if an image is captured with the high resolution of binning 1×1, then the image cannot be displayed on the monitor unless the reduction process is applied as shown in FIG. 2. This reducing process will degrade the image quality with the interpolation process. So, the image will have to be captured again. This will be an image capture by wasting the X-ray irradiating dose. Thus, even if the image is captured with a high resolution, the image cannot be displayed with the resolution higher than the monitor's resolution. Therefore, the image should be captured with the resolution considering a display magnification. On the other hand, if the capture is performed so as to adapt the monitor display by binning 2×2, then we can avoid wasting interpolation and X-ray irradiation, and it will not be necessary to make a capture frame rate low. However, it is necessary to set the captured conditions that each user desires and to control whole process from the condition of image display to the condition of sensor driving in order to minimize the effect by the image interpolation process at the image display. Hereafter, the embodiment in the present invention will be described referring to drawings.

Figure 3:
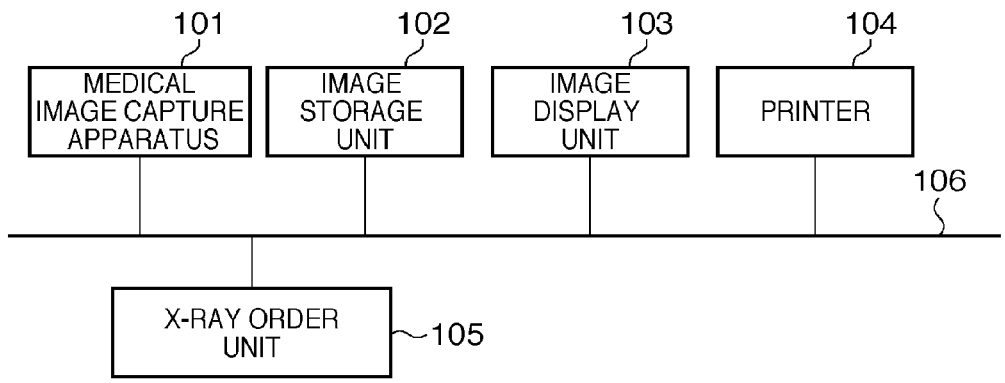
FIG. 3 illustrates a block diagram of a medical image capture system according to an embodiment of the invention.

FIG. 3 illustrates a block diagram indicating the arrangement of a medical image capture system. A medical image capture system 101 performs X-ray capture. This is as presented by an X-ray CT or MR apparatus and sometime called "modality". An image storage unit 102 stores captured images and is sometimes called "PACS" (for "Picture Archiving and Communications Systems"). An image display unit 103 displays images for image diagnosis. A printer 104 prints X-ray images on films or papers. The printer 104 may not be needed in the case of film-less operation. An X-ray order unit 105 is a unit to issue a image capture order and sometime called "RIS" (for "Radiology Information Systems"). The above apparatus and units are interconnected via a network 106.

Figure 4:
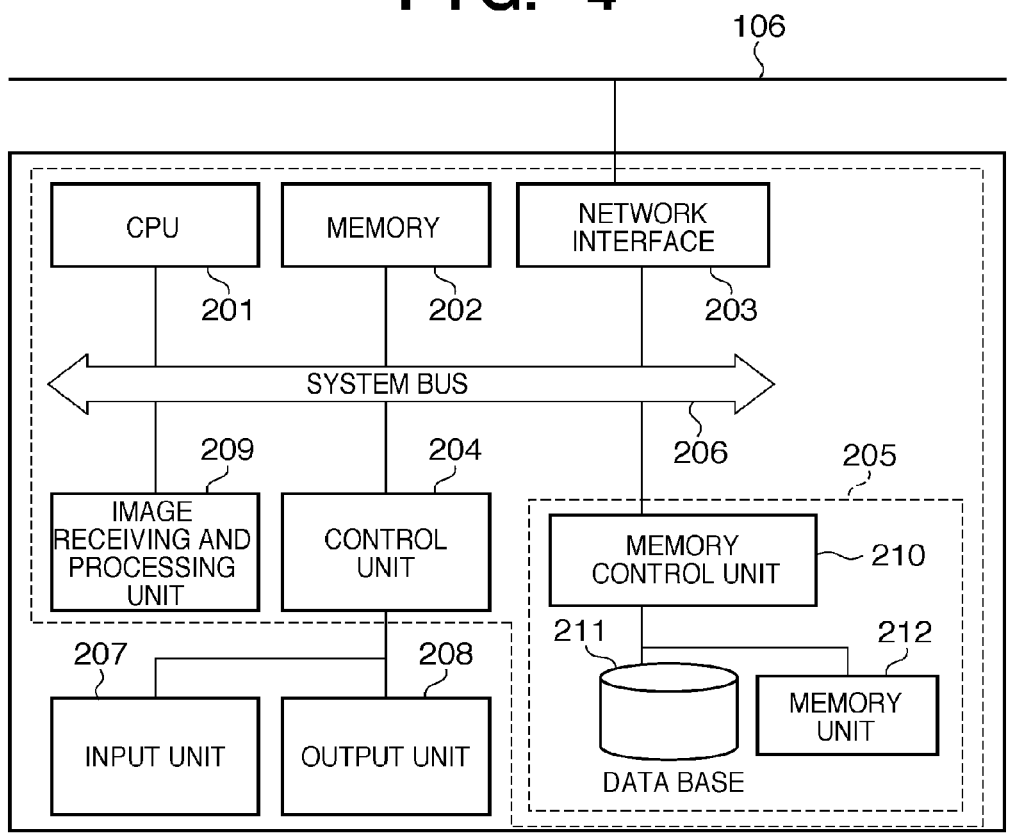
FIG. 4 shows a block diagram of a computer system in the invention.

FIG. 4 is a block diagram of a computer system used in this invention.

A control unit 21 of the medical image capture apparatus in this embodiment can be implemented by executing computer programs of a computer system (hardware) as shown in FIG. 4. As illustrated in FIG. 4, the control unit 204 controls CPU 201, a memory 202, a network interface 203, an input unit and an output unit 208. Further, a memory apparatus 205 comprises a database 211 which stores patient information and image information, and a memory control unit 210 which controls a memory unit 212 of storing image data. The arrangement is such that an image receiving and processing unit 209, the control unit 204 and the memory apparatus 205 are interconnected via a system bus 206 and can be communicated. The network interface 203 is connected to the network 106. Further, such computer system can be realized by LSI or ASIC (not shown in figures). Process resource in this computer system contains data communication band resource, CPU resource, GPU process resource, hard disk writing resource and network resource and other resource.

Figure 5:
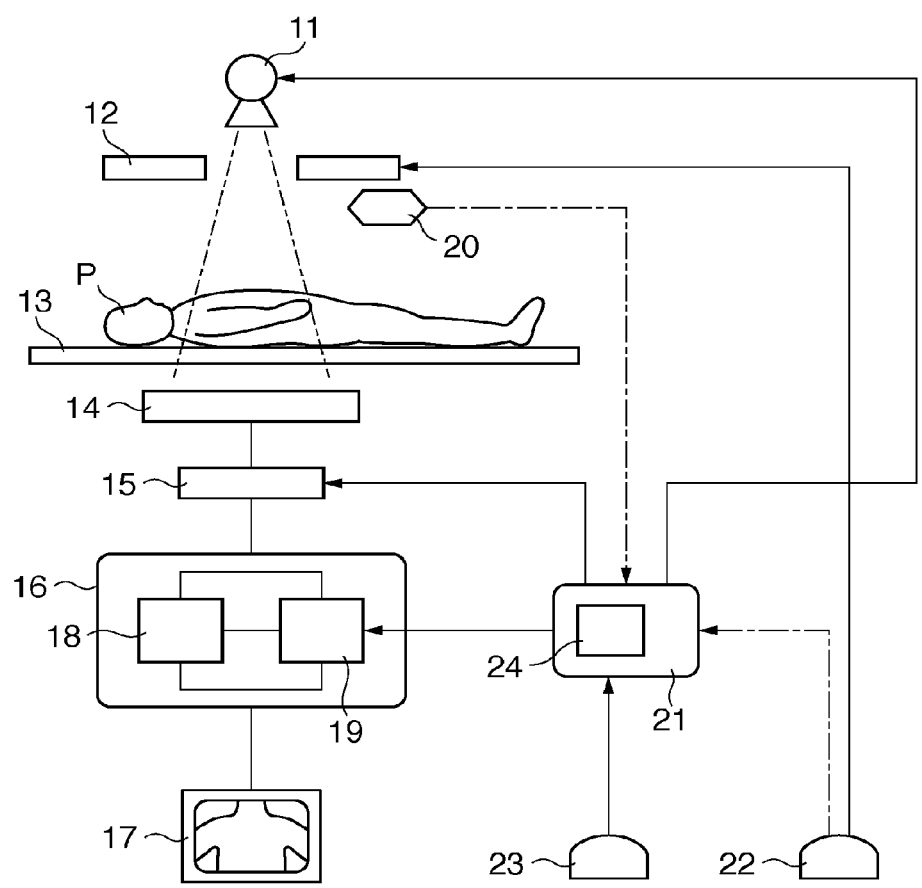
FIG. 5 illustrates the outline of a medical image capture apparatus.

FIG. 5 is a block diagram indicating the outline of the medical image capture apparatus. As shown in this figure, there is an X-ray aperture 12 which determines an X-ray irradiating area, in front of an X-ray tube 11 which irradiates the subject P with X-rays, the subject P being the object of examination. Further, a top panel 13 on which the subject P lies is placed under the X-ray aperture, and X-lay plane detection unit 14, which detects the transmissive X-rays transmitted through the subject P, is further placed under the top panel 13.

The output of X-ray plane detector 14 is connected to a readout circuit 15 for read out the image data from the X-ray plane detector 14. Further, the readout image data is sent to the image processing unit 16 to process the image. The image data after processing is sent to the display 17 and visualized on the TV monitor and etc. Further, the image processing unit 16 comprises a memory section 18 for storing the image data and a calculation section 19.

An open-degree detection means 20 for detecting open-degree of the X-ray aperture 12 is placed near the X-ray aperture 12, and the output of the open-degree means 20 is connected to control unit 21. Also, the X-ray aperture 12 is connected to the output of the irradiating area setting means 22, and the output of the irradiating area setting means 22 is further connected to the control unit 21.

An input means 23 of receiving the input of each control parameters with respect to capturing and executing designated operations is connected to the control unit 21, and the control unit has a memory section 24. Further, the output of the control unit 21 is the X-ray tube 11, the readout circuit 15 and the calculation section 19.

The each distance among the X-ray tube 11, the subject P, the top panel 13 and the X-ray plane detector 14 on the orientation of irradiating X-ray is respectively adjusted before capturing, and is fixed during capture. In addition, in this case the control unit 21 controls the X-ray generator and X-ray plane detector. However, the X-ray generator and X-ray plane detector may be respectively controlled by each of control sections divided the control unit 21 by two. Further, the control unit 21 may be realized by executing programs in a computer system (hardware), for example, which is configured with CPU 210 as shown in FIG. 4.

Figure 6:
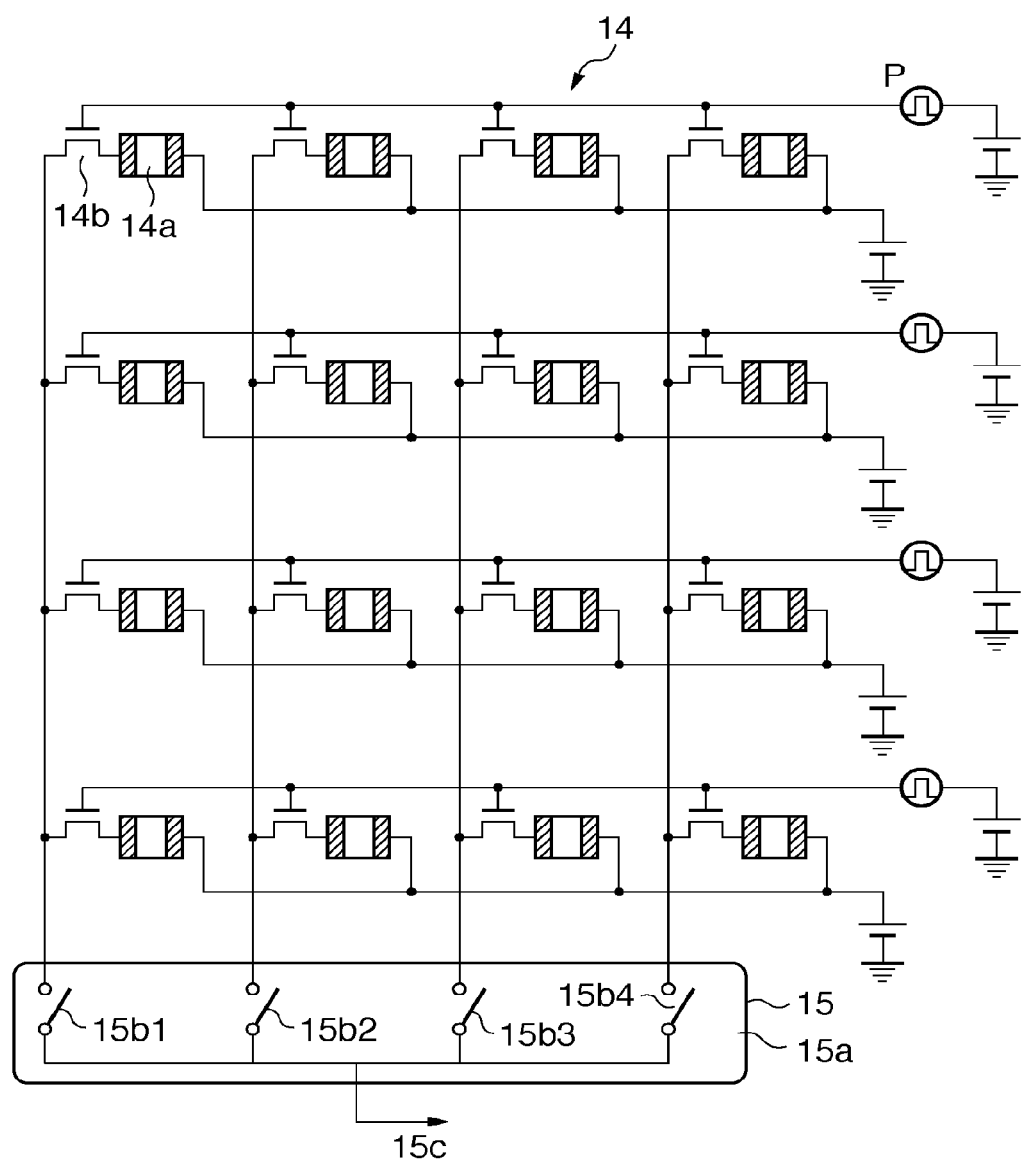
FIG. 6 shows arrangement and operations of an X-ray plane detection unit and readout circuit.

FIG. 6 illustrates a conceptual figure with respect to arrangement and operations for the X-ray plane detector and readout circuit. When the X-rays transmitted through the subject P impinge on the X-ray plane detector 14, the transmissive X-rays are converted to light with a fluorescent plane, not shown in the figure. Next, the converted light is further converted with photoelectric elements 14a which are arranged in two dimensions, and generates electric charge corresponding to the strength of the light. Then, the X-ray image of the subject P is converted to an electrical charge distribution in two dimensions by storing the electrical charge in a charge section inside the photoelectric element 14a.

After this conversion, a transfer pulse P is sent to a TFT (Thin Film Transistor) of a transfer section 14b which is comprised in a top column of each photoelectric element 14a, where a switching signal is input to the transfer section 14b. Then, the charge stored in the photoelectric element 14a is transferred to a switch 15b of a multiplexer 15a through the transfer section 14b of the readout circuit 15. Further, the switch 15b makes a connection one by one in the order 15b1, 15b2, - - - , and finally the charge is transferred to a signal out 15c, and the readout for one line of the top column is completed. The readout image signal is converted to digital image data via an amplifier, A/D converter, etc., not shown in the figure.

As mentioned above, one after another the transfer pulses are sent to the columns from the top to the bottom, and the connection is made with synchronization of the transfer pulse P in the switch 15b of the multiplexer 15a. In this manner, the whole image covered with the X-ray plane detector 14 is read out, and the X-ray image is stored in the memory section 18 of the image processing unit 16 as digital image data.

Normally, the more detailed captured images are required in the diagnosis by capturing a specific portion of the subject P when the region to be captured is set narrow. For example, if a portion to be captured is near the heart, there are situations such that the region of interest such as growth is desired to specify by narrowing the region to be captured in the whole image of chest region, or the region of interest is required to observe more in detail.

Figure 7:
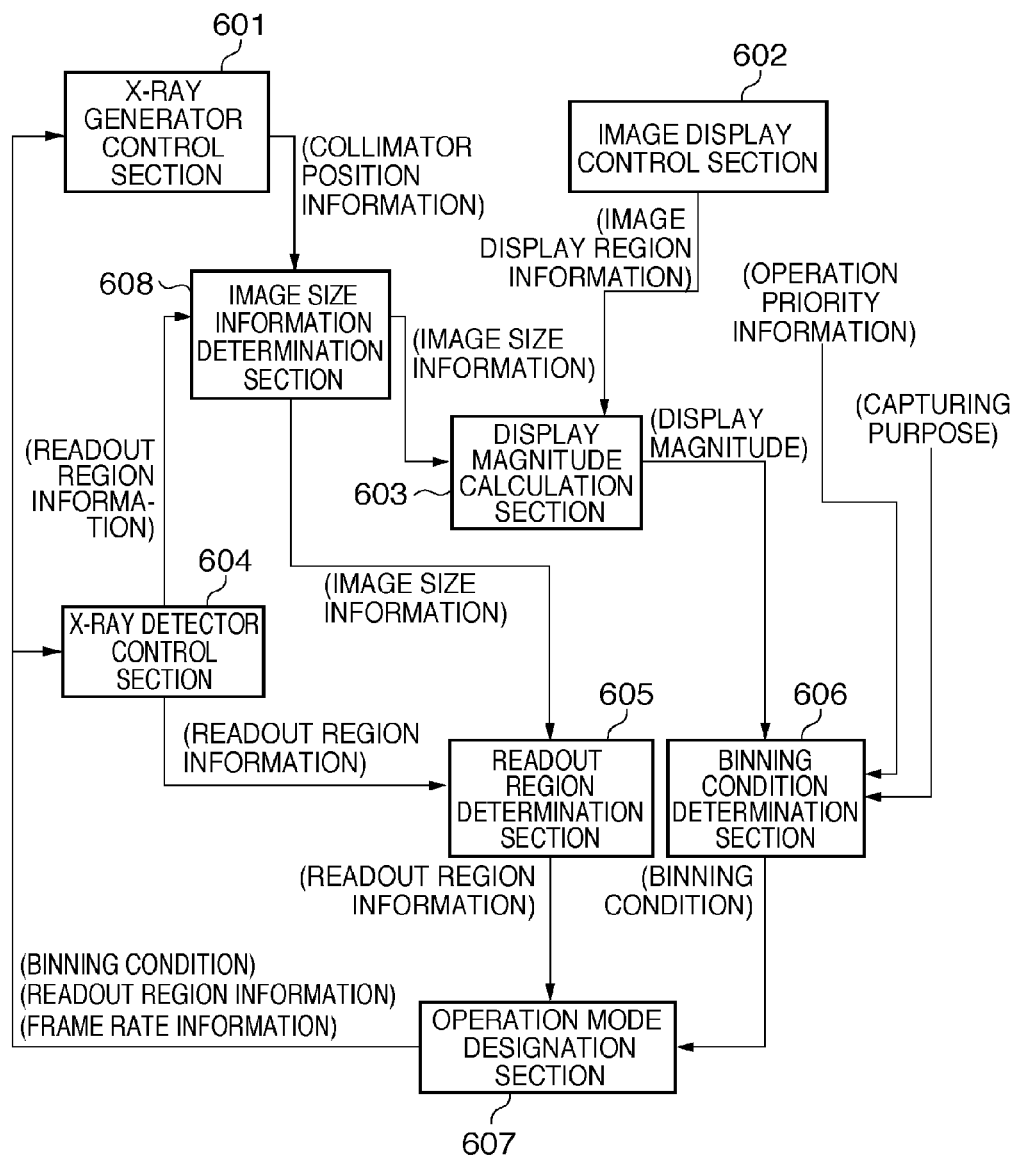
FIG. 7 shows a functional block diagram of controlling X-ray generator.

FIG. 7 shows a functional block diagram for controlling the X-ray generator.

First, the X-ray generator control section 601 controls the X-ray generator. An image display control section 602 controls display operation and display information for the display section 17 in FIG. 5. An image size information determination section 608 determinates an image size using collimating position information by an X-ray generator control section 601 and the readout information by an X-ray detector control section 604. Next, a display magnification calculation section 603 calculates a display magnification using this image size information and image display region information by the image display control section 602. Further, a reading area determination section 605 determines a reading area using image size information and a reading area information by the X-ray detector control section 604. A binning condition determination section 606, which comprises a priority determination section, acquires operation priority information and determines a binning condition using the operation priority and the display magnification by the display magnification calculation section 603. Further, an operation mode designation section 607 designates an operation mode determined by the reading area information and the binning condition to the X-ray generator control section 601 and X-ray detector control section 604.

Figure 8:
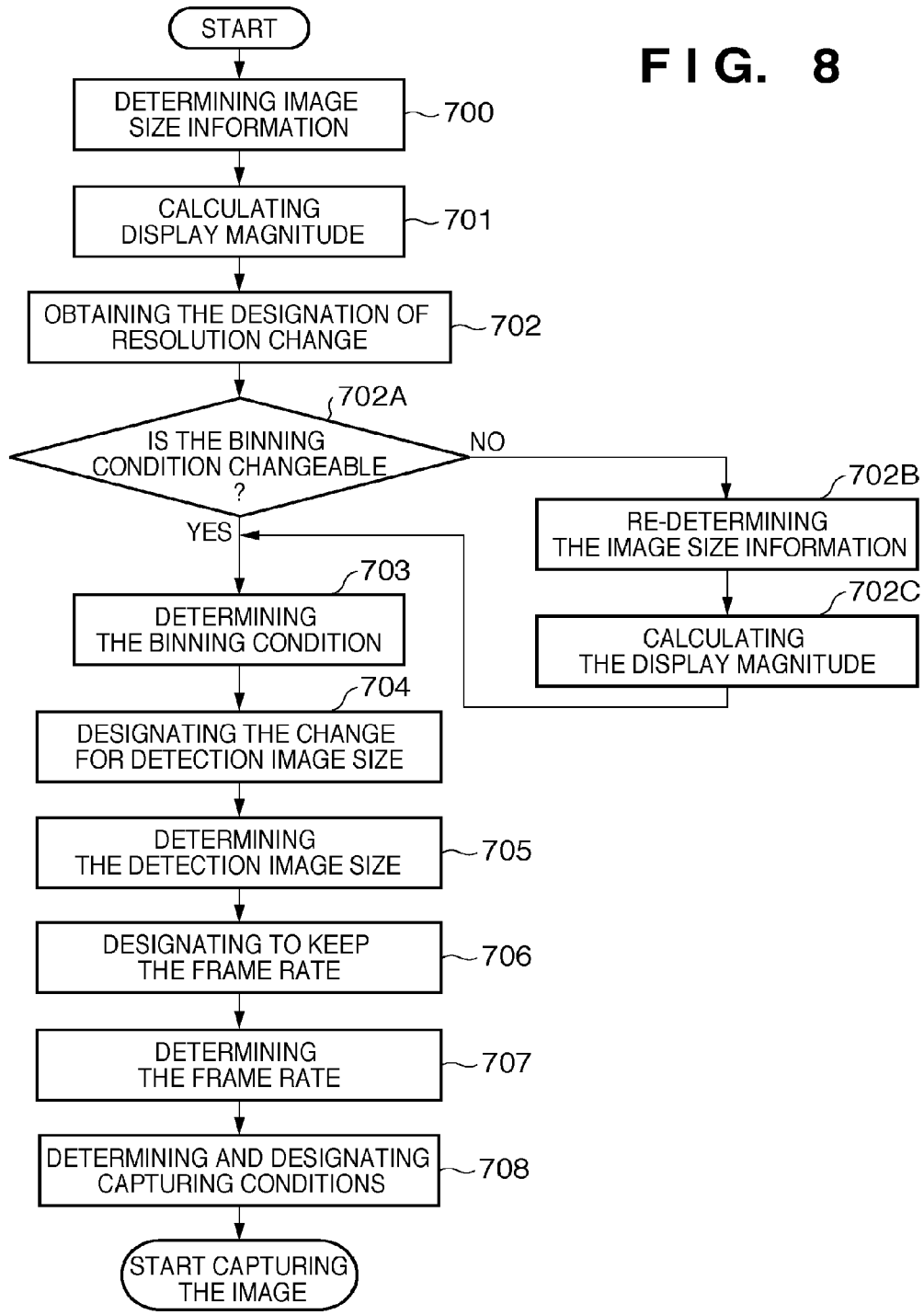
FIG. 8 shows a flowchart indicating operations in the first embodiment.

FIG. 8 shows a flowchart indicating operations in the first embodiment. Here, a series of the following steps will be executed based on designation of the control unit 21 having CPU. Further, an example such that a user inputs, as required, priority designations of a resolution and a reading area, and designation of a frame rate in accordance with the order shown in the flowchart, will be described in this flowchart.

In step 700, an image size is determined. The image size information is determined using collimating position information by an X-ray generator control section 601 and the reading area information by an X-ray detector control section 604.

The collimator is an aperture mechanism to determine the irradiating area of X-ray, where the effective region as an image is restricted because the irradiating area is limited by narrowing the irradiating area. The region which is limited is called image size information. Therefore, the image size is determined by the collimator position information which is acknowledged from the X-ray generator control section. If the collimator position information this time is different from that last time, the irradiating area to the X-ray detector is determined in accordance with the collimator position information acknowledged this time.

Further, a driving condition of the X-ray detector contains information of a reading area. The reading area is determined by a driving condition of the X-ray detector such as a whole region of the sensor, a condition for 14 inches (height)×17 inches (width), or a condition of 9 inches (height)×9 inches (width). An image size can be are preliminarily determined using the reading area because what is read out from the reading area is treated as the image data. There are examples of determining the image size using the condition of the driving condition such that the image size is determined by using the reading area and the information regarding the image size such as the image size, 2208×2688 corresponding to the driving condition, 14 inches×17 inches or by counting the number of pixels in both height and width directions using the reading area and pixel pitch of the sensor. The information of image size is determined by selecting the smaller value from the collimator position information or the reading area information of X-ray detector.

FIG. 11 shows the collimator aperture and a reading area. In this example, the driving condition is assumed to be a whole region of the X-ray plane detector 14, and elements indicated by 12a, 12b, 12c and 12d are assumed to be X-ray apertures. As the result of irising with a series of the apertures, a region to which the X-ray irradiates becomes a region 1002. Further, assuming that the driving condition in the current case is the region 1001, the X-ray plane detector (reading area) is a region 14 and the X-ray irradiating area is a region 1002. In this case, the image size information is assumed to indicate the region 1002.

In addition, some X-ray generator control section does not give notice of the collimation position information. In such case, the reading area information is treated as the image size information. Further, the image size may be determined by extracting the irradiating area from the image to be captured with image processing although the image size is not determined before capturing.

In step 701, the display magnification is calculated as a first display magnification if the image is displayed by using the image size information and the image display region information in current condition. How to calculate the first display magnification is as follows: The image size information is acquired in the image size information determination section 608, and the image display region information is acquired in the image display control section 602. The image display region information is an image region which can be displayed on the monitor.

For example, the image region can be displayed is determined in accordance with the display resolution of the current monitor when the image is displayed on the whole region of the monitor. In other application such that the image, patient information and other related information are displayed on the whole region of the monitor, a part of the whole display region of the monitor for the patient information and other related information is preliminarily set, and the whole display region except the set region is determined as the region for the image.

A display magnification calculation section 603 calculates a display magnification using the image size information and image display region containing the number of image pixel information, which gives a display area which does not exceed the number of the image display region, and which becomes a maximum display area for displaying the image based on the image size information. Thus, the display magnification calculation section 603 calculates the magnification which can most largely display the image in keeping the ratio of the height and width of the image.

FIG. 9 shows an example relationship between the image size information and image display region information. For example, it is assumed that the image size is 2000 (height)× 2500 (width), and the image display region is 1000 (height)× 1000 (width). In this case, if the height were scaled by 0.5 and the width scaled by 0.4, the image could be displayed on a whole image display region of the monitor. However, the ratio of the height and width of the original image should be kept on the image on the display. Therefore, the smaller magnification, 0.4 must be selected, and then the image size of 800 (height) and 1000 (width) will be displayed on the monitor. Thus, the magnification in this case is 0.4.

At step 702, a priority acquiring means in the binning condition determination section 606 acquires a resolution change order, and determines whether the higher resolution can be achieved by changing the binning condition. The resolution change is one of operation priorities. As mentioned above, there are various operation priorities which depend on the operator's request or capture purpose.

For example, if the portion to be captured moves quickly, as is the case with the heart, for example, a narrow field of view and a high speed capture will be desired. Also, if the portion to be captured does not move largely (for example, like the head) but the body part is required with high resolution capture, a wide field of view and magnified capture will be desired. Further, in the transmissive mode for positioning the position to be captured, even if a low resolution is selected, the high speed, wide field of view and high sensitivity (increasing the number of the binning) will be desired. Also, when an objective portion is captured, the wide dynamic range, high field of view and a high resolution will be desired.

As mentioned above, the operation priority is determined by the desire for a resolution. This operation priority may be determined by registering these optional patterns and selecting one of these patterns, or may be flexibly switched so as to selecting each operation priority requested by users as shown in a flowchart of FIG. 8.

FIG. 10 shows a summary of operation priorities. For example, in the transmissive capture of positioning, a low resolution can be set although the wide field of view, and high speed are required for positioning the capture position. The list shown in FIG. 10 is a typical example, so various combinations of these operation priorities can be freely configured. Further, if the user does not want the capture conditions changed automatically, the combination can be configured so as not to be changed automatically.

The list in FIG. 13 indicates the classifications for the case that the binning is changeable or the case that the binning is not changeable when the resolution is changed. In this embodiment, the resolution change is defined performed by changing the binning condition. Whether or not the binning condition can be changed depends on the purpose of the image capture. As the example of a changeable binning condition, there is a case such that the suitable image is displayed on the monitor in real time such as transmissive capture, where the image is not required to store. On the other hand, as the example of a fixed binning condition (or not changeable binning condition), there is a case like serial radiography capture or cineradiography such that the image is stored and is diagnosed and observed later. Therefore, these capture purposes are preliminarily input to the binning condition determination section 606. Further, these capture purposes are preliminarily input to the imaging apparatus. When the binning condition determination section 606 receives the resolution change order, it determines whether or not the preset binning condition is changeable based on the capture purpose.

In step 702A, if the binning condition determination section 606 determines that the binning condition is changeable, the control proceeds to step 702B. In step 702B, the image size information determination section 608 changes the collimator position information of the X-ray generator control section 601 and the reading area information of the X-ray detector control section 604 and calculates the image size again, assuming that the binning condition is temporarily changed corresponding to the resolution change order. For example, in FIG. 10, the image size is 2000 (Height)×2500 (width). Assuming that the binning condition was 1×1 in this case and the condition is changed to 2×2, the number of pixels in the height and width becomes a half of the number, 1000 (height)×1250 (width).

In step 702C, the display magnification calculation section 603 calculates a display magnification as a second display magnification as calculating at step 701. Assuming that the binning condition is changed to high sensitive (large binning number), 2×2, and then the image size becomes 1000 (height)×1250(width). Then considering the second display magnification, the size in height should be scaled by 1 and the size in width be scaled by 0.8 in order to display the image. Therefore, the smaller number, 0.8 is selected for the display magnification. Thus, the image, 800 (height)×1000 (width) is displayed on the monitor, where the image is acquired by respectively multiply the height and width by 0.8.

In step 703, the binning condition determination section 606 determines the binning condition. If the binning condition is not changeable, the binning condition is used as is.

If the binning condition is changeable in step 702A, the image size information is determined again in step 702 and further the display magnification is re-calculated as the second magnification v step 702C.

Here, if the binning condition is changed, the binning condition determination section 606 compares both the display magnifications before and after changing the binning condition. Then, the binning condition whose display magnification is closer to one is selected. In the example in FIG. 10, if the binning condition is 1×1, then the corresponding first display magnification is 0.4. On the other hand, if the binning condition is 2×2, then the corresponding second display magnification is 0.8. Therefore, the binning condition whose display magnification is closer to one is 2×2 and the binning condition is determined as 2×2.

Thus, even if the image is captured with a high resolution, the effect of the high resolution will be lost after the captured image size is reduced so as to be displayed on the monitor. When the resolution is changed, the binning condition is changed and if the display magnification based on the changed binning condition is closer to one, then the changed binning condition is adopted. If the display magnification is not close to 1, then the original binning condition is adopted. Thus as described above, the substantial resolution on the monitor can be enhanced and the frame rate of driving the sensor or the reading area can be flexibly changed by changing from low sensitivity to high sensitivity of the binning conditions.

In step 704, a detected image size change order is acquired to change the detected image size in the reading area. In step 705, responding to the detected image size change order, the detected image size is temporarily changed, and the display region, in a case where the detected image with the temporarily changed detected image size is displayed on the monitor, is calculated using the selected binning condition and display magnification, and then whether or not the display region can be placed within a display frame of the monitor. In step 705, if the display region is equal to or smaller than a display frame of the monitor, the size of reading area by X-ray is changed in accordance with the detected image size change order.

The operation priority contains a reading area priority. The reading area priority is classified into the priority which can change the reading area condition and the priority which cannot change it. The reading area priority, which can change the reading area condition, contains a wide region priority and narrow region priority. FIG. 13 illustrates the classification of these regions. The reading area of X-ray plane detector is determined by the driving condition of the X-ray plane detector. For example, the different size of region can be gradually read out by changing the driving condition of the X-ray plane detector. The reading areas are configured so as to switch to a various size such as 14 inches×17 inches, 12 inches×12 inches and 9 inches×9 inches.

Here, if the temporarily changed display region of the detected image is larger than the frame regardless of receiving the change order at step 704, the detected image size is determined to be not changeable. In this case, the preset detected image size is selected. If the temporarily changed display region of the detected image is equal to or smaller than the frame, the reading area condition is determined to be changeable. In this case, the image size in the binning condition determined at the step 703 will be determined with the reading area condition of the wide region when changing to the wide region, and determined with the reading area condition of the narrow region when changing to the narrow region. As described above, if the changed image size is smaller than the preset image size, the driving condition of X-ray plane detector may be changed to the wide region or narrow region.

As well as the request for changing the resolution change in step 702, the requirement for holding a frame rate is dependent on the operator's request or the capture purpose. Assume that the frame rate holding order is acquired corresponding to the above request.

In step 706, if the frame rate holding order is acquired from the operator, at least one of the detected image size and binning condition is temporarily changed while holding the current frame rate so as to enlarge the signal reading area from the X-ray detector or to change the resolution of signal reading area to the higher resolution. Further, if the display region of the detected image, which is calculated by using the detected image size and the binning condition based on the temporary change and the display magnification selected by the selection means, is equal or smaller than the frame size of the monitor, then the detected image size and the binning condition based on the temporary change are selected. FIG. 13 illustrates an example of the reading area, binning and frame rate. For example, regarding the small reading area, 9 inches×9 inches, FIG. 13 shows that the binning 4×4 is changeable to the binning 1×1 while holding the current frame rate 5 fps to display on the monitor image region.

In step 707, the frame rate determination means in the operation mode designation section 607 finally determines the frame rate. As described above, the frame rate is determined by the relation with the size of the reading area of driving sensor and the set value of the binning.

FIG. 12 shows an example of the relation of the frame rate is determined by the relation with the size of the reading area of driving sensor and the set value of the binning. Referring to FIG. 12, when the reading area becomes wider, it is not possible to select the high frame rate. Further, even in the same reading area, when the binning is larger, it is possible to select the high frame rate. If the frame rate is not changeable, the conditions are determined by original frame rate. If the frame rate is changeable, the conditions are determined corresponding to the frame rate priority. If the high frame rate priority is active, then using the high frame rate, the conditions are determined so as to satisfy with the conditions described in FIG. 12. For example, assuming that the binning condition is 2×2, the reading area is 12 inches×12 inches and the frame rate is 5 fps, if the frame rate priority indicates high frame rate priority, then the frame rate can be increased up to 15 fps. As described, the conditions are determined by changing the frame rate.

In step 708, the operation mode designation section 607 determines the capture condition and designates it. The capture conditions are comprised by the frame rate of X-ray, the reading area information of the X-ray plane detector, the binning conditions of the X-ray plane detector, and so on.

As described above, in this embodiment, first the image size information is determined and the priority is acquired.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-180050, filed Jul. 31, 2009, which is hereby incorporated by reference herein in its entirety.

What is claimed is:

1. An imaging apparatus comprising:
    an X-ray detector for detecting transmissive X-rays passing through a subject irradiated with X-rays from the imaging apparatus;
    an image display unit for displaying the detected image detected by said X-ray detector;
    a display magnification calculation unit for calculating a display magnification of the image display based on information of the detected image size which is a size of a reading area of said X-ray detector and a display frame size of said image display; and
    a setting unit for setting a binning condition of said X-ray detector based on the display magnification.

2. An imaging apparatus according to claim 1, further comprising a changing unit for temporarily changing a size of the reading area and calculating a display region when displaying the detected image of the temporary changed detected image size on said image display unit corresponding to a request for changing a detected image size, and changing the size of reading area by the X-rays in accordance with the request for changing a detected image size if the display region is equal to or smaller than the display frame size of said image display unit.

3. An imaging apparatus according to claim 1, further comprising a control unit for temporarily changing at least one of the detected image size and binning condition while holding the current frame rate so as to enlarge the signal reading area from said X-ray detector or to change the resolution of signal reading area to the higher resolution if the frame rate holding order is acquired from the operator, and if the display region of the detected image, which is calculated by using the detected image size and the binning condition based on the temporary change and the display magnification selected by said selection means, is equal or smaller than the frame size of the monitor, then selecting the detected image size and the temporary changed binning condition.

4. A method of controlling an imaging apparatus having a X-ray detector for detecting transmissive X-rays passing through a subject irradiated with the X-rays from the imaging apparatus and an image display unit for displaying the detected image by the X-ray detector, comprising the steps of:
    calculating a display magnification of the image display based on information of the detected image size which is a size of a reading area of the detector and a display frame size of the image display; and
    setting a binning condition of the X-ray detector based on the display magnification.

5. A non-transitory computer-readable storage medium storing a computer program for causing a computer to execute each step of a method of controlling an imaging apparatus defined in claim 4.

* * * * *